United States Patent [19]
Aoki et al.

[11] Patent Number: 5,441,536
[45] Date of Patent: Aug. 15, 1995

[54] METHOD FOR THE PRODUCTION OF AN IMPLANT HAVING AN APATITE COATING LAYER USING A HYDROTHERMAL TREATMENT

[75] Inventors: Hideki Aoki, Tokyo; Masaru Akao, Kawasaki; Yoshiharurayama Shin, Higashimurayama; Osamu Hayashi, Fuchu; Masahiko Yoshizawa, Sagamihara, all of Japan

[73] Assignee: Kabushiki Kaisya Advance, Tokyo, Japan

[21] Appl. No.: 969,227

[22] PCT Filed: Jun. 16, 1992

[86] PCT No.: PCT/JP92/00769

§ 371 Date: Feb. 12, 1993

§ 102(e) Date: Feb. 12, 1993

[87] PCT Pub. No.: WO92/22335

PCT Pub. Date: Dec. 23, 1992

[30] Foreign Application Priority Data

Jun. 18, 1991 [JP] Japan ................... 3-242899

[51] Int. Cl.⁶ .................... A61F 2/02; C23C 22/00
[52] U.S. Cl. ..................... 427/2.27; 623/16; 623/66
[58] Field of Search ............... 427/2; 623/11, 16, 18, 623/66

[56] References Cited

U.S. PATENT DOCUMENTS

| | | | |
|---|---|---|---|
| 4,871,578 | 10/1989 | Adam et al. | 427/2 |
| 4,882,196 | 11/1989 | Shimanune et al. | 427/2 |
| 4,960,646 | 10/1990 | Shimamune et al. | 428/471 |
| 5,141,576 | 8/1992 | Shimamune et al. | 148/254 |

FOREIGN PATENT DOCUMENTS

| | | |
|---|---|---|
| 02858263 | 10/1988 | European Pat. Off. |
| 0407698A1 | 1/1991 | European Pat. Off. |
| 3709457A1 | 10/1987 | Germany |
| 58-39533 | 8/1983 | Japan |
| 59-51485 | 12/1984 | Japan |
| 63-38443 | 2/1988 | Japan |
| 63-160666 | 7/1988 | Japan |

*Primary Examiner*—David Isabella
*Attorney, Agent, or Firm*—Finnegan, Henderson, Farabow, Garrett & Dunner

[57] ABSTRACT

An implant is produced by coating a core material with a calcium phosphate type compound and converting the coating layer into an apatite type ceramic layer by a hydrothermal treatment.

5 Claims, No Drawings

METHOD FOR THE PRODUCTION OF AN IMPLANT HAVING AN APATITE COATING LAYER USING A HYDROTHERMAL TREATMENT

TECHNICAL FIELD

The present invention relates to a method for the production of an implant.

BACKGROUND ART

The following methods have been typically known as ways of coating a metallic substrate with hydroxyapatite.

(1) A plasma spraying method using hydroxyapatite as a starting material (see, for example, KOKAI (Japanese Unexamined Patent Publication) No. 58-39533, KOKAI No. 62-34566).

(2) A method comprising the steps of preparing a powder formed mainly of a calcium salt and a phosphorus salt as a starting material, applying a coating film of the powder onto a metallic substrate by the plasma spraying technique, and immersing the coated metallic substrate in an atmosphere of steam or in water thereby converting the powder film into hydroxyapatite (see, for example, KOKAI No. 63-93851).

(3) A method comprising the steps of applying to the surface of a metallic substrate an organic-solvent coating liquid having an organic calcium compound and an organic phosphorus compound dissolved therein and heating and firing the coated metallic substrate thereby forming a hydroxyapatite coating film on the metallic substrate (thermal decomposition method) (see, for example, KOKAI No. 64-86975).

The method (1) mentioned above which uses hydroxyapatite as the starting material for plasma spraying proceeds through the steps of heating and cooling because of the operating principle of plasma flame spraying and tends to submit the hydroxyapatite to decomposition and, therefore, entails the following problems.

(a) Alkali components such as calcium oxide and tetracalcium phosphate persist as residues in the coating film.

(b) An amorphous phase occurs in the coating film.

(c) Since the alkali components and the amorphous layer mentioned above have high degrees of solubility and the coating layer of hydroxyapatite (HAP) itself succumbs to solution readily, the produced composite poses the problem of betraying deficiency in lasting biostability, yields to embrittlement in the course of solution, possibly suffers from a lopical increase in pH in a living body, and entails a problem of biocompatibility.

(d) Regarding the HAP layer, since the IR absorption spectrum of the-produced composite after separation therefrom of the HAP layer in a crushed form shows no discernible absorption peak originating in the hydroxyl group, this HAP layer does not deserve to be called a stoichiometric hydroxyapatite and poses the problem of offering no sufficient chemical stability.

The method (2) mentioned above has the problem of not only rendering it difficult to form a single apatite phase from the calcium salt and phosphorus salt by the solid phase reaction recording to the plasma spraying technique but also submitting the reaction to the onset of decomposition. Even the immersion in an atmosphere of steam or in water lends no impetus to the reaction for conversion into a single hydroxyapatite phase but entails the disadvantage that the formation of calcium carbonate and other substances ensues, the solution advances, and the coating layer embrittles.

The thermal decomposition method (3) mentioned above, similarly to the plasma spraying method, has the problem of tending to form an amorphous phase of calcium oxide and tetracalcium phosphate and rendering it difficult for the coating layer to be converted into a single phase of stoichiometric hydroxyapatite. And, owing to the fact that the substrate itself is fired in the open air, this method also has the problem of giving rise to an oxide coating layer between the substrate and the HAP coating layer and, depending upon the firing conditions, the oxide coating layer becomes brittle and when the HAP coating layer is completely dissolved in a living body and consequently exposed to the vital tissue, inducing the occurrence of macrophage and foreign giant cells and causing a foreign reaction.

Besides the methods cited above, methods such as sputtering and chemical vapor deposition are available for the coating of a metallic substrate with hydroxyapatite. These methods, however, have not been technically established as evinced by the fact that they experience great difficulty in obtaining calcium phosphate of high crystallinity.

DISCLOSURE OF THE INVENTION

Accordingly, an object of the present invention is to provide a method for quick and accurate production of an implant having an apatite type ceramic coating layer formed on the surface of a core material (substrate).

Other objects and advantages of the present invention will become apparent from the following description.

In accordance with the present invention, there is provided a method for the production of an implant which comprises coating a core material with a calcium phosphate type compound and then converting the coating layer, by a hydrothermal treatment, into an apatite type ceramic layer.

BEST MODE FOR CARRYING OUT THE INVENTION

In the light of the true state of the prior art described above, the present invention has succeeded in perfecting a method for producing an implant having as an outermost layer or coating layer thereof an accurate and stable stoichiometric hydroxyapatite and apatite type ceramic layer by forming on a core material (substrate) a coating layer of a calcium phosphate type compound by the process of, for example, plasma spraying, thermal decomposition, or sputtering and then submitting the resultant coated core material to a hydrothermal treatment. In the present invention, the terms "coating" and "coating film" are used synonomously.

In accordance with the method of production contemplated by the present invention, a calcium phosphate coating layer is first formed on the surface of a core material (substrate) by the process of, for example, plasma spraying, thermal decomposition, or sputtering. Then, the coating layer is hydrothermally treated in an aqueous solution simultaneously containing calcium ion and phosphate ion or an aqueous calcium phosphate solution or distilled water at a temperature in the range of, for example, between 80° C. and 200° C. for a period of between 0.5 and 100 hours. The material which has undergone this hydrothermal treatment has had the crystal structure thereof transformed into hydroxyapatite, which is confirmed by the X-ray diffraction process to constitute a single hydroxyapatite phase of very high crystallinity and is found by the IR absorption process and the Raman spectroscopy method to have a clear absorption by the hydroxyl group. The coating layer produced in the manner described above is an extremely stable chemical as evinced by the fact that it is substantially equal in solubility in physiological saline solution or simulated humor to a sintered stoichiometric hydroxyapatite article having the same surface area.

When the calcium phosphate coating layer which has been formed by any of the processes cited above is subsequently treated hydrothermally in the same manner as described above in a solution simultaneously containing a metallic ion such as an alkali metal ion or alkaline earth metal ion and an anion of carbonic acid, nitric acid, sulfuric acid, boric acid, or halogen ion or in a solution containing any of the above-mentioned ions alone, it is converted into a material of apatite structure containing the relevant ions mentioned above. Thus, a novel implant material conforming to a particular purpose of use can be obtained.

The term "implant" as used in the present invention refers to substitutes, prosthetics, reinforcements, etc., for such hard vital tissues as artificial roots of teeth, artificial bones, and bone plates, etc.

The core material (referred to occasionally as "substrate" or "basic plate"), though variable in shape with the kind of implant aimed at, is made of a metallic material such as Ti type alloy or stainless steel or ceramic material.

The calcium phosphate type compounds which are effectively usable in the method of the present invention include, for example, $\alpha$- and $\beta$-tricalcium phosphates (TCP), octacalcium phosphate, and amorphous calcium phosphate. These calcium phosphate type compounds can be used either alone or in any mixture thereof.

The formation of the calcium phosphate type coating layer may be attained by any of conventional processes such as, for example, plasma spraying process, baking process, thermal decomposition process, sputtering process, CVD process, and PVD process. It does not need to be limited to any specific coating means.

The "hydrothermal treatment" involved in the method of the present invention refers to a procedure which comprises immersing a calcium phosphate-coated implant material in water such as an aqueous solution simultaneously containing calcium ion and phosphate ion, hermetically sealing the immersed implant material (in an atmosphere of such inert gas as air, nitrogen, or argon gas), and heating the sealed immersed implant material. By this treatment, the coating layer is enabled to be formed of a more stoichiometric hydroxyapatite. The term "stoichiometric hydroxyapatite" as used herein refers to $Ca_{10}(PO_4)_6(OH)_2$.

The conditions employed for the hydrothermal treatment and the solution used for the treatment are variable With a particular species of apatite layer aimed at. For the purpose of mainly producing a single hydroxyapatite layer, this hydrothermal treatment is desired to be performed in a solution simultaneously containing calcium ion and phosphate ion or an aqueous calcium phosphate solution or distilled water at a temperature of 200° C. or less, preferably falling in the range between 90° C. and 150° C., for a period of 100 hours or less, preferably falling in the range between 6 and 72 hours.

In the present invention, the preparation of the components of the solution for the hydrothermal treatment and the setting of the temperature of treatment and the period of treatment (hereinafter these factors of the hydrothermal treatment may be occasionally referred to collectively as "environment of hydrothermal treatment") are easy to attain. Thus, a varying species of apatite layer conforming to a particular purpose of use can be produced.

The apatite type ceramic produced by the method of the present invention is such that the apatite type ceramic layer is allowed to have part of the metallic ions other than Ca and the anions other than $PO_4$ or OH (hydroxyl group) substituted by adjusting the components such as of the aqueous solution to be used for the hydrothermal treatment mentioned above. Optionally, the coating layer may be formed of an apatite type ceramic substance (such as, for example, strontium apatite, magnesium apatite, chlorine apatite, fluorine apatite, or carbonate apatite) other than hydroxyapatite.

EXAMPLES

The present invention will now be further illustrated by, but is by no means limited to, the following Examples.

Example 1

A $\alpha$-tricalcium phosphate (TCP)-metal composite material was obtained by forming a calcium phosphate coating layer on a metallic substrate (metal: titanium) by the plasma spraying process using TCP powder as the starting material for spraying. The composite material thus obtained was immersed in an aqueous solution simultaneously containing $Ca^{2+}$ and $PO_4^{3-}$ ions at a pH value of 9.0 (which may be in the range of a pH of 6 to 12) (or in an aqueous calcium phosphate solution having a pH value in the range of 5.5 to 12.5), hermetically sealed, and subjected to a hydrothermal treatment at a temperature of 120° C. (which may be in the range between 80° C. and 200° C.). The duration of this treatment was 24 hours (generally within 100 hours). This hydrothermal treatment brought about transformation of crystal structure of the TCP layer into a HAP layer. By the X-ray powder diffraction process and the infrared absorption spectrometry process, it was confirmed that the HAP layer formed a more stoichiometric chemically stable composition.

Example 2

A calcium phosphate coating layer was formed on a metallic substrate (metal: titanium) by the thermal decomposition process using a calcium salt and a phosphoric ester. The resultant composite material was fired at 500° C., a temperature not so high as to induce intense oxidation of the metallic substrate, for five hours to effect thorough combustion of existent carbon sources. The composite material thus obtained was immersed in an aqueous solution simultaneously containing $Ca^{2+}$ and $PO_4^{3-}$ ions at a pH value of 7.5 (generally pH 6–12) (or in an aqueous calcium phosphate solution having a pH value in the range of 5.5 to 12.5), hermetically sealed, and hydrothermally treated at a temperature of 120° C. (generally in the range between 80° C. and 200° C.). The duration of this treatment was 12 hours (generally within 100 hours). By the X-ray powder diffraction process and the infrared absorption spectrometry process, it was confirmed that the HAP layer in the composite material that underwent this hydrothermal treatment was formed of a more stoichiometric chemically stable composition.

Example 3

A TCP-metal composite material was obtained by forming a calcium phosphate coating layer on a metallic substrate (metal: stainless steel) by the plasma spraying process using TCP powder as the starting material for spraying. The composite material thus obtained was subjected to a hydrothermal treatment in a calcium carbonate sol. The temperature of this treatment was 120° C. (generally in the range between 80° C. and 200° C.) and the duration of the treatment was 48 hours (generally within 100 hours). By the infrared absorption spectrometry process and the powder X-ray diffraction process, it was confirmed that, in consequence of the treatment described above, there was produced a composite material comprising an apatite coating layer having carbonic acid partially substituted at the position of the hydroxyl group of the hydroxyapatite structure and a metallic substrate.

Example 4

An $\alpha$-TCP sprayed layer-metal composite material was obtained by plasma spraying an $\alpha$-TCP or $\beta$-TCP powder as the starting material for spraying on a metallic substrate (metal: stainless steel). The composite material thus obtained was immersed in an aqueous solution simultaneously containing $Ca^{2+}$ and $PO_4^{3-}$ ions at a pH value of 7.0 (generally in the range between pH 6 and 12) (or in an aqueous calcium phosphate solution having a pH value in the range of 5.5 to 12.5), hermetically sealed, and hydrothermally treated at a temperature of 120° C. (generally in the range between 80° C. and 200° C.). The duration of-this treatment was 30 hours (generally within 100 hours). By the X-ray powder diffraction process and the infrared absorption spectrometry process, it was confirmed that the hydrothermal treatment caused transformation of crystal structure of the $\alpha$-TCP layer into a HAP layer having a more stoichiometric chemically stable composition.

By controlling the duration of the hydrothermal treatment (for example, 1.5 hours at 120° C. in an aqueous solution simultaneously containing $Ca^{2+}$ and $PO_4^{3-}$ ions at a pH value in the range between pH 6 and 12), there was obtained a composite material having the transformation into the HAP produced only in the surface region of the layer.

Example 5

The surface of a Ti base intended for the root of a tooth was coarsened by sand blasting (or bead blasting or acid treatment) and subjected to plasma spraying using a $\beta$-TCP powder having a particle size distribution of 30 to 60 $\mu$m to form a coating layer of $\alpha$-TCP thereon. In a HAP gel prepared by dissolving in water a HAP synthesized by a wet process, the coated base was immersed in such a manner as to keep the HAP particles from directly contacting the artificial root of a tooth and then subjected to a hydrothermal treatment at 120° C. for 30 hours. Consequently, there was obtained a composite material having the coating layer thereof transformed from the $\alpha$-TCP layer into a HAP layer (confirmed by the X-ray powder diffraction process and the infrared absorption spectrometry process).

The apatite type ceramic layer to be produced by the hydrothermal treatment is required to be formed at least in the outermost layer. Of course, the coating lay may be wholly formed of the apatite type ceramic substance.

INDUSTRIAL APPLICABILITY

As described above, the method of according to the present invention for the production of an implant enables an apatite type ceramic layer represented by a chemically stable hydroxyapatite layer to be produced without resorting to the process of producing a calcium phosphate coating layer. By varying the environment of hydrothermal treatment, there can be formed an apatite type ceramic layer having part of the metallic ions and anions thereof substituted. Since the transformation of crystal structure is effected very quickly and accurately, the method permits mass production of the implant. The present invention, therefore, provides very high economic utility.

We claim:

1. A method for the production of an implant, consisting essentially of coating a core material with at least one calcium phosphate type compound selected from the group consisting of $\alpha$-tricalcium phosphate and $\beta$-tricalcium phosphate by plasma spraying to form a coating layer on the core material and then, converting said coating layer into an apatite type ceramic layer by subjecting the coated core material to a hydrothermal treatment at a temperature of from 120° C. to 200° C. for from 0.5 to 100 hrs.

2. The method of claim 1, wherein said core material is a metallic substrate formed of a material selected from the group consisting of titanium, a titanium type alloy, stainless steel, a cobalt-chromium type alloy, and a nickel-titanium type alloy.

3. The method of claim 1, wherein said hydrothermal treatment is carried out in an aqueous solution that contains Ca ions and $PO_4$ ions and has a pH value of from 6 to 12 at a temperature of from 120° C. to 150° C.

4. The method of claim 1, wherein said hydrothermal treatment is carried out in an aqueous calcium phosphate solution having a pH value of from 5.5 to 12.5 at a temperature of from 120° C. to 150° C.

5. The method of claim 1, wherein said hydrothermal treatment is carried out for from 12 to 100 hrs.

* * * * *

UNITED STATES PATENT AND TRADEMARK OFFICE
CERTIFICATE OF CORRECTION

PATENT NO. : 5,441,536
DATED : August 15, 1995
INVENTOR(S) : Hideki Aoki et al.

It is certified that error appears in the above-indentified patent and that said Letters Patent is hereby corrected as shown below:

On the title page, item [75], change "Yoshiharurayama" to
--- Yoshiharu ---.

Signed and Sealed this

Twenty-sixth Day of December, 1995

Attest:

BRUCE LEHMAN

*Attesting Officer*      *Commissioner of Patents and Trademarks*